United States Patent [19]

Meglasson

[11] Patent Number: 5,599,841
[45] Date of Patent: Feb. 4, 1997

[54] USE OF 3-GUANIDINOPROPIONIC ACID IN THE TREATMENT AND PREVENTION OF METABOLIC DISORDERS

[75] Inventor: Martin D. Meglasson, Kalamazoo, Mich.

[73] Assignee: The Upjohn Company, Kalamazoo, Mich.

[21] Appl. No.: 101,350

[22] Filed: Aug. 2, 1993

Related U.S. Application Data

[63] Continuation of Ser. No. 935,621, Aug. 26, 1992, abandoned, which is a continuation of PCT/US91/01109, Feb. 27, 1991, abandoned, which is a continuation-in-part of PCT/US91/00334, Jan. 22, 1991, abandoned, which is a continuation-in-part of Ser. No. 486,615, Feb. 28, 1990, abandoned.

[51] Int. Cl.$^6$ .................... A61K 31/19; A61K 31/195; A61K 31/155
[52] U.S. Cl. .................... 514/557; 514/565; 514/634
[58] Field of Search .................... 514/557, 565, 514/634

[56] References Cited

U.S. PATENT DOCUMENTS 3,843,798  10/1974  Cook .................... 424/319

FOREIGN PATENT DOCUMENTS

| 891509 | 1/1972 | Canada . |
|---|---|---|
| 1153424 | 5/1969 | United Kingdom . |
| 1195199 | 6/1970 | United Kingdom . |
| 1195200 | 6/1970 | United Kingdom . |
| 1552179 | 9/1979 | United Kingdom . |

OTHER PUBLICATIONS

A. Aynsley–Green and K. G. M. M. Alberti, "*In Vivo Stimulation of Insulin Secretion by Guanidine Derivatives in the Rat*", Horm. Metab. Res. 6:115–120 (1974).

F. Blachier, et al., "*Stimulus–Secretion Coupling of Arginine–Induced Insulin Release. Uptake of Metabolized and Nonmetabolized Cationic Amino Acids by Pancreatic Islets*", Endocrinology 124(1):134–141 (1989).

J. J. Roberts and J. B. Walker, "*Feeding a Creatine Analogue Delays ATP Depletion and Onset of Rigor in Ischemic Heart*", Am. J. Physiol. 243:H911–H916 (1982).

T. S. Moerland, et al., "*Administration of a Creative Analogue Induces Isomyosin Transitions in Muscle*", Am. J. Physiol. 257:C810–C816 (1989).

E. A. Shoubridge, et al., "*Biochemical Adaptation in the Skeletal Muscle of Rats Depleted of Creatine with the Substrate Analogue β–Guanidinopropionic Acid*", Biochem. J. 232:125–131 (1985).

D. A. MaHanna, et al., "*Effects of β–Guanidinopropionic Acid on Murine Skeletal Muscle*", Exper. Neurol. 68:114–121 (1980).

R. P. Shields, et al., "*Skeletal Muscle Function and Structure After Depletion of Creatine*", Lab. Invest. 33(2):151–158 (1975.

J. V. Otten, et al., "*Thyrotoxic Myopathy in Mice: Accentuation by a Cratine Transport Inhibitor*", Metabolism 35(6):481–484 (1986).

D. S. Grosso, et al., "*Characterization of a Carrier–Medicated Transport System for Taurine in the Feta Mouse Heart In Vitro*", J. Clin. Invest., E61(4):944–952 (1978).

*Primary Examiner*—Raymond Henley, III
*Assistant Examiner*—Kevin Weddington
*Attorney, Agent, or Firm*—Lawrence T. Welch

[57] ABSTRACT

The present invention provides a method for treating or preventing certain metabolic disorders comprising the systemic administration of 3-guanidinopropionic acid.

4 Claims, No Drawings

USE OF 3-GUANIDINOPROPIONIC ACID IN THE TREATMENT AND PREVENTION OF METABOLIC DISORDERS

CROSS REFERENCE TO RELATED PATENT APPLICATIONS

This application is a continuation of U.S. Ser. No. 07/935,621, filed 26 Aug. 1992, now abandoned, which is a continuation of international application PCT/US91/01109, filed 27 Feb. 1991, now abandoned, which is a continuation-in-part of international application PCT/US91/00334, filed 22 Jan. 1991, now abandoned, which is a continuation-in-part of U.S. Ser. No. 07/486,615, filed 28 Feb. 1990, now abandoned.

FIELD OF INVENTION

The present invention provides a new use for known compounds. More particularly, the present invention provides a method of treating or preventing certain metabolic disorders of human and animal metabolism, e.g., hyperglycemia, impaired glucose tolerance, hyperinsulinemia, insulin insensitivity, hyperamylinemia, excess adiposity or hyperlipidemia by the administration of 3-guanidinopropionic acid (3-GPA).

BACKGROUND OF THE INVENTION

There are several metabolic disorders of human and animal metabolism, e.g., hyperglycemia, impaired glucose tolerance, hyperinsulinemia and insulin insensitivity, hyperamylinemia, excess adiposity, and hyperlipidemia. Some or all of the above disorders may occur in the following disease states: non-insulin dependent diabetes mellitus (NIDDM), obesity, hypertension and atherosclerosis.

Hyperglycemia is a condition where the blood glucose level is above the normal level in the fasting state, following ingestion of a meal, or during a provocative diagnostic procedure, e.g., a glucose tolerance test. It can occur in NIDDM as well as obesity. Hyperglycemia can occur without a diagnosis of NIDDM. This condition is called impaired glucose tolerance or pre-diabetes. Impaired glucose tolerance occurs when the rate of metabolic clearance of glucose from the blood is less than that commonly occurring in the general population after a standard dose of glucose has been orally or parenterally administered. It can occur in NIDDM as well as obesity, pre-diabetes and gestational diabetes.

Hyperinsulinemia is defined as having a blood insulin level that is above normal level in the fasting state, following ingestion of a meal or during a provocative diagnostic procedure. It can be seen in NIDDM or obesity and can be associated with or causal in hypertension or atherosclerosis. Hyperinsulinemia can occur without a diagnosis of diabetes. It may occur prior to the onset of NIDDM. Insulin insensitivity, also called insulin resistance, occurs when the insulin-dependent glucose clearance rate is less than that commonly occurring in the general population during diagnostic procedures such as a hyperinsulinemic clamp [See, e.g., DeFronzo, R. A. et al., Am. J. Physiol. 232: E214–E233, (1979)] or a minimal model test. See, e.g., Bergman, R. N. et al., J. Clin. Invest. 68: 1456–1467 (1981). Insulin insensitivity is considered also to occur when the blood glucose concentration is higher than that commonly occurring in the general population after intravenous administration of insulin (insulin tolerance test) or when the ratio of serum insulin-to-glucose concentration is higher than that commonly occurring in the general population after a 10–16 hour fast. Insulin insensitivity may be found in NIDDM or obesity and can also be associated with or causal to hypertension or atherosclerosis.

Hyperamylinemia is defined as having an abnormally high blood amylin level. Amylin is also known as diabetes associated peptide (DAP) and insulinoma associated polypeptide (IAP). Hyperamylinemia can be seen in NIDDM or obesity.

Excess adiposity can be seen in NIDDM associated with obesity as well as obesity without NIDDM. It is defined as a higher fat body mass-to-lean body mass ratio than that commonly occurring in the general population as measured by whole body specific gravity or other generally accepted means.

Hyperlipidemia is defined as having an abnormal level of lipids in the blood. Hyperlipidemia exists when the serum concentration of total cholesterol or total triglycerides or the serum concentration of LDL-cholesterol/HDL-cholesterol is higher than that commonly occurring in the general population. It can be seen in NIDDM or atherosclerosis.

The above disease states could be treated by either ameliorating or preventing the metabolic and biochemical disorders. In addition, humans and animals, which have not been diagnosed as having one of the above disease states but evidencing some or all of the disorders described above, could be benefitted by preventing the development of a currently recognized disease state. Therefore, a compound that is useful in the treatment of hyperglycemia, impaired glucose tolerance, hyperinsulinemia, insulin insensitivity, hyperamylinemia, excess adiposity or hyperlipidemia could also be used to treat or prevent NIDDM, obesity, hypertension or atherosclerosis.

3-Guanidinopropionic acid (3-GPA) is an endogenous metabolite found in animals and humans. See, e.g., Hiraga, Y. et al., J. Chromatography 342: 269–275 (1985) and Watanabe, Y. et al., *Guanidines*, edited by Mori et al., Plenum, N.Y., pp. 49–58 (1983). The compound, which is available from Sigma Chemical Co., has been used extensively in the study of creatine metabolism [See, e.g., Walker, J. B., Adv. Enzymol. 50: 177–242 (1979)] and gamma-aminobutyric acid receptor function. See, e.g., Bowery, R. et al., Br. J. Pharmacol. 50: 205–218 (1974). Except as noted below, these studies do not relate to 3-GPA's utility in treating human or animal disease.

Guanidine, monoguanidine and diguanidine compounds have been shown to produce hypoglycemia. See, e.g., Watanabe, C., J. Biol. Chem. 33: 253–265 (1918); Bischoff, F. et al., Guanidine structure and hypoglycemia 81: 325–349 (1929). However, these compounds were observed to be toxic. In 1957, biguanide derivatives, e.g. phenformin and metformin, were used clinically as anti-diabetic agents. Some members of this class continue to be used today while others have been withdrawn from the market or banned in the United States and most Western countries. See, e.g., Schafer, G., Diabete Metabol. (Paris) 9: 148–163 (1983).

Gamma-guanidinobutyramide also known as Tyformin, and the HCl salt of Tyformin, known as Augmentin, were investigated as potential anti-diabetic agents from the mid-1960's until the mid-1970's. While Augmentin produced hypoglycemia, it was reported to produce hypertension in dogs [See, e.g., Malaisse, W. et al., Horm. Metab. Res. 1: 258–265 (1969)] and respiratory and circulatory collapse in rats and rabbits. See, e.g., Buckle, A. et al., Horm. Metab. Res. 3: 76–81 (1971). The free acid of the amide was said to lack hypoglycemic activity [See, e.g., Beeson, M. et al., Horm. Metab. Res. 3: 188–192 (1971)].

British patent 1,153,424 discloses the use of certain esters and amides of guanidino-aliphatic acids in the treatment of diabetes mellitus where hyperuremia is present. The patent does not disclose that these compounds have an effect on hyperglycemia or any other symptom or pathological state related to diabetes. In a Canadian patent, 891509, the use of esters and amides of guanidinoaliphatic acids were disclosed for treating hyperuremia and hyperglycemia in diabetes mellitus. As noted above, the biologic activity of a guanidino alkanoic acid was known to be different and less favorable so as to be ineffective compared to its amide for treating hyperglycemia.

British patent, 1,195,199 discloses the use of guanidino alkanoic acids or their amides or esters in an insulin-containing, parenterally-administered composition for the treatment of hyperglycemia occurring in diabetes. According to this patent, the combining of a guanidino alkanoic acid, amide or ester with insulin reduces the risk of hypoglycemia as compared to insulin alone. British patent 1,195,200 discloses the use of guanidino alkanoic acids in a composition containing a guanidino alkanoic acid amide or ester derivative for the treatment of hyperglycemia occurring in diabetes. In a subsequent British patent, 1,552,179, the use of guanidino alkanoic acids, their salts, amides or esters in combination with a gluconeogenesis inhibitor for treating hyperglycemic conditions was disclosed. Metformin was cited as an inhibitor of gluconeogenesis. Biological data indicated that HL 523, the preferred guanidino alkanoic acid derivative, was inactive as a single agent in six of seven experiments where blood glucose concentration was measured in alloxan diabetic mice and only weakly active in the seventh study. Most notably, British patents 1,195,199, 1,195,200 and 1,552,179 do not claim utility for guanidino alkanoic acids, as the sole active component, in compositions for treating hyperglycemic symptoms in diabetes. Among the guanidino alkanoic acids tested, several were inactive as a single agent. Thus, a variety of guanidino alkanoic acids lack significant antidiabetic activity and combination of these compounds with an agent of known anti-diabetic activity, e.g., metformin, is necessary to show beneficial activity.

Aynsley-Green and Alberti injected rats intravenously with 3-GPA, arginine, guanidine, 4-guanidinobutyramide, and 4-guanidinobutyric acid. Arginine and 3-GPA stimulated insulin secretion transiently, but did not affect the blood glucose concentration while the other compounds stimulated insulin secretion but produced a rise in blood glucose concentration. See, e.g., Aynsley-Green, A. et al., Horm. Metab. Res. 6: 115–120 (1974). Blachier, et al., observed that 10 mM 3-GPA stimulated insulin secretion by isolated rat islets in vitro. See, e.g., Blachier, F. et al., Endocrinology 124: 134–141 (1989). The insulin response induced by 3-GPA was 55 % of that occurring when arginine was tested at the same concentration. In rats fed a diet supplemented with 10 mg/g 3-GPA for 30–60 days, the heart glycogen content was increased. See, e.g., Roberts, J. et al., Am. J. Physiol. 243: H911–H916 (1982). Similarly, skeletal muscle glycogen content was increased in rats fed chow supplemented with 10mg/g of 3-GPA for 6–10 weeks. Mice fed a diet supplemented with 3-GPA at 20 mg/g and supplied with drinking water containing 5 mg/ml 3-GPA for 7–12 weeks had serum glucose concentrations that did not differ significantly from mice receiving unsupplemented chow and water. See, e.g., Moerland, T. et al., Am. J. Physiol. 257: C810–C816 (1989).

With respect to adiposity, it is known that in some, but not all cases [See, e.g., Shoubridge, E. et al., Biochem. J. 232: 125–131 (1985)], supplementation of the diet with 10–20 mg/g 3-GPA results in decreased body weight. See, e.g., Moerland, supra and Mahanna, D. et. al., Exper. Neurol. 68: 114–121 (1980). This effect has been attributed to decreased skeletal muscle mass and has not been attributed to reduced adiposity or decreased lipid storage. See, e.g., Mahanna, supra and Shields, R. et al., Lab. Invest. 33: 151–158 (1975).

What is needed in the art is a sole therapy to treat or prevent the underlying metabolic disorders in these conditions.

INFORMATION DISCLOSURE STATEMENT

The following patents disclosed the use of guanidino-aliphatic acids or their amides or esters for the treatment of insulin-dependent diabetes: British patent 1,153,424; Canadian patent 891509; British patent 1,195,199; British patent 1,195,200; British patent 1,552,179. None of these patents disclosed the use of 3-GPA as a sole therapy, nor as a sole active agent in a pharmaceutical composition. 3-GPA has been shown to stimulate insulin secretion without lowering blood glucose, See, e.g., Ansley-Green, A. et al., Horm. Metab. Res. 6: 115–120 (1974) and Blachier, F., Endocrinology 124: 134–141 (1989); and to increase heart glycogen content. See, e.g., Roberts, J., Am. J. Physiol. 243: H911–H916 (1982) and Moerland, T., Am. J. Physiol. 257: C810–C816 (1989). It is also known that supplementation of the diet with 3-GPA results in decreased body weight. See Shoubridge, E. A. et al., Biochem. J. 232: 125–131 (1985); Moerland, supra; Mahanna, D. A. et al., Exper. Neurol. 68: 114–121 (1980); and Shields, R. P. et al., Lab. Invest. 33: 151–158 (1975). All of the references cited in this section are discussed above.

SUMMARY OF THE INVENTION

The present invention provides a method of treating or preventing a metabolic disorder selected from the group consisting of hyperglycemia, impaired glucose tolerance, hyperinsulinemia, hyperamylinemia, excess adiposity and/or hyperlipidemia in a patient susceptible to or experiencing said disorder comprising the systemic administration of 3-guanidinopropionic acid or a pharmacologically acceptable salt thereof.

Despite extensive suggestions in the literature that it would be ineffective as a sole therapy for insulin-dependent diabetes, surprisingly and unexpectedly, it has been found that 3-GPA causes several biologic effects that are beneficial in the treatment of human disease. It improves plasma glucose level, insulin sensitivity, plasma amylin level, adiposity and plasma lipid level. All of these effects are beneficial in treating NIDDM. 3-GPA offers therapeutic advantage over metformin, a compound currently used to treat NIDDM. See, e.g., Vigneri, R. et al., Diabetes Care 10: 118–122 (1987). When administered to KKA$^y$ (lipjohn) diabetic mice, 3-GPA is more potent and produces a greater decrease in plasma glucose concentration.

3-GPA is ineffective when administered to rodents in a state similar to insulin-dependent diabetes mellitus. 3-GPA did not alter the non-fasting plasma glucose level in lean, normoglycemic C57BL6Job/? mice (Jackson Laboratory) when administered as a 2 mg/g admixture in chow for 13 days. At a higher level, 10 mg/g, 3-GPA did not affect plasma glucose concentration when administered to C57BL6Job/? mice for 4 days, but after administration for 13 days, plasma glucose concentration was decreased. The dose of 3-GPA that produced lower plasma glucose levels in C57BL6Job/? mice was >6g/kg body weight/day. By contrast, a much lesser dose (130 mg/kg/d) produced an antihyperglycemic effect in diabetic KKA$^y$ mice. Since, 3-GPA decreases plasma glucose levels that are elevated, but has little effect at normal plasma glucose concentration, 3-GPA has a great therapeutic benefit in that it ameliorates hyperglycemia with little risk of hypoglycemic reactions in case of overdose.

NIDDM is characterized by hyperglycemia in the fasting or post-prandial state and impaired glucose tolerance after oral or parenteral administration of a glucose solution. 3-GPA, that has been administered to KKA$^y$ mice, a rodent model of NIDDM, decreases the non-fasting plasma glucose concentration and improves glucose tolerance. The minimum effective dose in KKA$^y$ mice is 130 mg/kg/d when administered as an admixture in rodent chow. Higher doses produce a proportionately greater effect. Doses that are less than the minimum effective dose in KKA$^y$ mice may be effective at decreasing blood glucose levels in other species, e.g., human, since elimination is rapid in rodents and may occur more slowly in other species.

Impaired tissue insulin sensitivity and hyperinsulinemia occur in NIDDM [See, e.g., Defronzo, R., Diabetes 37: 667–687 (1988) and Reaven, G., Diabetes 37: 1595–607 (1988)], hypertension (See, e.g., Reaven, supra), obesity (See, e.g., Glass A., supra), and atherosclerosis [See, e.g., Reaven, supra and Stout, R. W., Diabetologia 16: 141–150 (1979)] and may be etiological factors in these diseases. 3-GPA ameliorates hyperinsulinemia in KKA$^y$ mice and decreases the plasma ratio of insulin-to-glucose concentration, indicating increased insulin sensitivity. Therefore, 3-GPA is useful in the treatment or in the prevention of NIDDM, hypertension, obesity, and atherosclerosis.

Hyperamylinemia may occur in NIDDM, decreasing tissue glucose metabolism [See, e.g., Leighton, B. et al., Nature 335: 632–635 (1988)] and altering pancreatic hormone secretion [See, e.g., Clark, A., Diabetic Medicine 6: 561–567 (1989)]. 3-GPA ameliorates hyperamylinemia and therefore is beneficial in treating disease states in which plasma amylin concentration is increased.

Excess adiposity is an etiological factor in NIDDM and when extreme, represents a disease state in itself. 3-GPA decreases adiposity by decreasing the level of lipids stored in fat and liver tissue. The compound is therefore beneficial in the treatment of obesity alone or in concert with NIDDM. The effect of 3-GPA is selective for lipid-rich tissues (e.g., epididymal fat and fatty liver of ob/ob mice) while muscle mass is unaffected or only minimally affected.

Increased serum low density lipoprotein (LDL) cholesterol concentration is an etiological factor in coronary artery disease. 3-GPA decreases LDL-cholesterol levels in spontaneously hyperlipidemic mice and therefore is useful in treating or preventing hyperlipoproteinemia, atherosclerosis and coronary artery disease.

By sole active pharmaceutical agent is meant that the 3-GPA compound or its salt, administered as claimed herein, is the only pharmaceutical agent in the composition.

By patients susceptible to or experiencing a metabolic disorder, i.e., hyperglycemia, impaired glucose tolerance, hyperinsulinemia, insulin insensitivity, hyperamylinemia, excess adiposity and/or hyperlipidemia is meant a human or animal who exhibits said metabolic disorder and is therefore likely to exhibit one of more of the disease states described above. Such patients are readily diagnosed by a physician or veterinarian of ordinary skill. By treatment is meant the amelioration or total avoidance of the metabolic disorder as described herein. By prevention is meant the avoidance of a currently recognized disease state, as described herein, in a patient evidencing some or all of the metabolic disorders described above.

For all of these purposes, any convenient route of systemic administration is employed, e.g., orally, parenterally, intranasally or intrarectally. In general, the preferred form of administration is orally.

The above compositions may be administered in a sustained release formulation. By sustained release is meant a formulation in which the drug becomes biologically available to the patient at a measured rate over a prolonged period. Such compositions are well-known in the art.

Since 3- GPA decreases body fat without affecting the lean mass, 3-GPA would be of great commercial benefit to the meat, poultry, and fish producing industries in achieving its goal of producing leaner animal products. 3-GPA may be administered admixed in the diet of farm animals or as a pharmaceutical preparation such as an oral tablet or capsule, by injection, or by implantable sustained release devices thereby increasing the protein content of the carcass while decreasing its fat content. This would produce muscle tissue with less fat. This benefit of 3-GPA would also impact on the potential health to the meat, poultry, and fish consuming public. The term "farm animals" is defined as animals which are raised for food production. The term includes, but is not limited to, such animals as cattle, poultry, fish, swine, and lamb.

3-GPA increases exercise tolerance in normal mice. Thus the present invention may be useful in treating muscular dysfunction, such as post-poliomyelitis chronic muscle fatigue syndrome or muscular dystrophy, or in treating chronic muscular weakness associated with advanced age or chronic immobilization, or in increasing endurance and exercise in normal humans.

3-GPA also improved the survival rate of mice maintained in a low oxygen environment and therefore is beneficial in treating or preventing disease states involving tissue hypoxia, e.g., peripheral claudication and exercise intolerance in diabetic humans, and angina, myocardial infarction and stroke in diabetic and normal humans.

It is known that glucose-dependent protein crosslinking alters the tertiary structure of several proteins. This protein glycosylation may contribute to diabetic complication and complications of aging in non-diabetic humans, such as neuropathy, nephropathy, retinopathy, hypertension, and atherosclerosis. 3-GPA is useful to block protein glycosylation and therefore be of benefit in treating or preventing this reaction.

The dosage regimen for 3-GPA in accord with this invention will depend on body weight. 3-GPA, in pharmaceutical dosage form, can range from 1–500 mg/kg/day. The preferred dose is 5–100 mg/kg/day. Any sustained released formulations can be used.

DETAILED DESCRIPTION OF THE INVENTION

The present invention is seen more fully by the examples given below.

EXAMPLE 1

Improvement of Plasma Glucose Level

To test the effect of 3-GPA on non-fasting plasma glucose concentration in KKA$^y$ mice, the mice are administered 3-GPA admixed in rodent chow for 4 days. Plasma is prepared from blood collected by puncturing the retroorbital sinus of conscious mice that are in the ad libitum fed state. Blood samples are obtained on day 0 (prior to treatment) and on day 4 of treatment. Plasma glucose is measured by an enzyme coupled assay using hexokinase and glucose-6-phosphate dehydrogenase. Data is shown as a means ±S.E.M. for 5 mice per group. Doses that produce a reduction in plasma glucose of 20% or greater are considered to have had a biologically meaningful effect. The percentage reduction in plasma glucose levels by 3-GPA is as follows: 0.8 mg/g, 20%; 1.5 mg/g, 48%; 2 mg/g, 52%; 10 mg/g, 77%. The results are summarized in Table I. 3-GPA also decreased the non-fasting plasma glucose level in obese, hyperglycemic C57BL6Job/ob mice which are considered to be a model of NIDDM.

To test the effect of 3-GPA on glucose tolerance in KKA$^y$ mice, the mice are administered 3-GPA admixed in rodent chow at 10 mg/g for 14 days or received unsupplemented chow. Blood samples are collected and plasma analyzed for glucose as described in legend to Table 1. Blood is collected at time 0 (prior to glucose administration) and at intervals after injection of 1.5 g/kg glucose intraperitoneally. Data, as seen in Table II, is shown as means ±S.E.M. for 5–6 mice per group.

EXAMPLE 2

Improvement in Insulin Sensitivity

Data supporting the utility of 3-GPA in improving insulin sensitivity and ameliorating hyperinsulinemia is shown in Table III. KKA$^y$ mice are fed chow supplemented with 10mg/g 3-GPA for 14 days or unsupplemented chow. Blood samples are obtained and analyzed for glucose as described in legend to Table I. Plasma insulin is determined using a single antibody radioimmunoassay technique. Data is shown as means ±S.E.M. for 5–6 mice/group.

EXAMPLE 3

Improvement of Plasma Amylin Level

KKA$^y$ mice receive 3-GPA as a 2 mg/g admixture in chow or unsupplemented chow for 4 days. Ob/ob mice receive 3-GPA as a 2 or 10 mg/g admixture in chow or unsupplemented chow for 30 days. Blood samples are obtained as described in Table I. Amylin is measured in plasma using a double antibody radioimmunoassay. Results are shown in Table IV.

EXAMPLE 4

Improvement in Adiposity

The effect of 3-GPA on body and organ weights is tested in ob/ob mice. The mice receive 3-GPA as a 2 mg/g or 10 mg/g admixture in chow or are fed unsupplemented chow. Data, which is seen in Table V, is shown as means ±S.E.M.

EXAMPLE 5

Improvement in Plasma Lipid Level

Ob/ob mice receive 3-GPA as a 10 mg/g admixture in chow for 13 days or are fed unsupplemented chow. Plasma for lipoprotein analysis is obtained as described in Table I. Lipoprotein levels are determined with a Demand Autoanalyzer. Data, which is shown in Table VI, is seen as means ±S.E.M. for 5 mice per group. For comparison, the plasma lipoprotein profile is shown for 4 lean, non-diabetic C57BL6Job/? mice that are untreated.

EXAMPLE 6

Reduced Adiposity and Body Weight in Non-diabetic Obese Mice

3-GPA is tested in A$^y$ mice obtained from Jackson Laboratories (Bar Harbor, Me.). Mice are determined to be free of glycosuria in the fed state using KetoDiaStix™. 3-GPA is administered for 14 days as an admixture in milled mouse chow at 2 and 5 mg/g chow or unsupplemented chow is provided. Lean and fat body mass is determined using the method of Pace and Rathbun. (See Pace, N. and Rathbun, E. N. Studies on Body Composition. III. The Body Water and Chemically Combined Nitrogen Content Relation to Fat Content. J. Biol. Chem 158: 658–691 (1945)). Body weights and the wet weights of excised organs are determined gravimetrically using an analytic laboratory balance.

As shown in Table 7, 3-GPA significantly decreases the body weight and fat mass of mice as percentages of the body weight, diaphragm and calf muscle, which are selected as representative sources of skeletal muscle, are significantly increased by 3-GPA. The total lean body mass (reflecting primarily skeletal muscle mass) is similarly increased by 3-GPA when expressed as a percentage of the body weight.

EXAMPLE 7

Effect of 3-GPA on Insulin Sensitivity and Body Weight in Adult Rhesus Monkeys 3-GPA is administered orally in gelatin capsule three times daily at a dose of 16 mg/kg for 11 days. Insulin sensitivity is determined using the Bergman Minimal Model technique (Pacini, G. and Bergman, R. N: MINMOD: a computer program to calculate insulin sensitivity and pancreatic responsivity from the frequently sampled intravenous glucose tolerance test, Computer Meth. Progr. Biomed. 23: 113–122, 1986). Insulin sensitivity was improved in all subjects. Body weight decreased in the two heaviest monkeys, but was unaffected in a low body weight monkey. These findings are consistent with previous data from obese rodents where 3-GPA decreased body weight by preferentially lowering the body fat mass without affecting the lean tissue mass and increased insulin sensitivity.

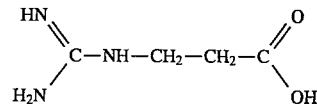

TABLE 1

| 3-GPA Admixture in Chow (mg/g) | Average dose (g/kg/d) | Non-Fasting Plasma Glucose (mg/dl) Days of Treatment | |
|---|---|---|---|
| | | 0 | 4 |
| Experiment 1 | | | |
| Nil | 0 | 481 + 59 | 651 + 52 |
| 2 | 0.32 | 441 + 68 | 313 + 75* |
| 10 | 1.74 | 464 + 67 | 148 + 5** |
| *, P = 0.006. **, P = 0.000. | | | |
| Experiment 2 | | | |
| Nil | 0 | 628 + 77 | 536 + 49 |
| 0.8 | 0.13 | 617 + 58 | 429 + 52* |
| 1.5 | 0.21 | 624 + 64 | 279 + 49** |

*, P = 0.17. **, P = 0.006

TABLE 2

| | Plasma Glucose (mg/dl) | | |
|---|---|---|---|
| Time (min) | Control | 3-GPA | P-value |
| 0 | 484 + 101 | 171 + 21 | 0.014 |
| 15 | 842 + 83 | 230 + 40 | 0.000 |
| 30 | 527 + 81 | 270 + 31 | 0.014 |
| 60 | 430 + 51 | 190 + 19 | 0.002 |
| 120 | 327 + 54 | 153 + 18 | 0.013 |

TABLE 3

| | Plasma Insulin (microunits/ml) | Plasma Insulin/Glucose (microunits/mg) |
|---|---|---|
| Control | 3,009 + 419 | 7.30 + 1.57 |
| 3-GPA | 299 + 117* | 2.04 + 0.83** |

*, P = 0.000; **, P = 0.016

TABLE 4

| Strain | Treatment | Plasma Amylin (ng/ml) |
|---|---|---|
| KKAy | control | 15.0 + 4.1 (n = 5) |
| | 3-GPA | 4.3 + 0.6 (n = 3) |
| ob/ob | control | 1.3 + 0.2 (n = 6) |
| | 3-GPA (2 mg/g) | 1.8 + 0.2 (n = 3) |
| | 3-GPA (10 mg/g) | 0.46 + 0.05 (n = 5) |

TABLE 5

| Experiment 1. 31 days treatment. 4–6 mice/group | | | |
|---|---|---|---|
| Concentration in Chow: | 0 | 2 mg/g | 10 mg/g |
| Body Weight (g) | 52.3 + 0.7 | 49.4 + 1.1 | 36.1 + 1.5 |
| Liver (g) | 4.3 + 0.2 | 3.6 + 0.1 | 1.6 + 0.2 |
| Epididymal Fat (g) | 3.7 + 0.1 | 3.8 + 0.3 | 2.5 + 0.2 |
| Experiment 2. 13 days treatment. 5 mice/group | | | |
| Concentration in Chow: | | 0 | 10 mg/g |
| Body Weight (g) | | 43.4 + 1.3 | 36.8 + 1.3 |
| Liver (g) | | 2.4 + 0.2 | 1.3 + 0.1 |
| Heart (g) | | 0.11 + 0.01 | 0.10 + 0.004 |
| Diaphragm (g) | | 0.065 + 0.004 | 0.061 + 0.004 |
| Calf muscle (g) | | 0.050 + 0.001 | 0.047 + 0.003 |

TABLE 6

| Phenotype: | ob/? | ob/ob | ob/ob | P-value |
|---|---|---|---|---|
| 3-GPA | (−) | (−) | (+) | ob/ob(−)vs(+) |
| Cholesterol: | | | | |
| Total | 114 + 4 | 213 + 12 | 214 + 7 | 0.932 |
| Alpha | 96 + 3 | 194 + 15 | 204 + 9 | 0.660 |
| Beta | 18 + 1 | 19 + 4 | 10 + 3 | 0.044 |
| Triglyceride | | | | |
| Total | 112 + 10 | 170 + 41 | 149 + 25 | 0.656 |
| Alpha | 70 + 3 | 87 + 4 | 99 + 9 | 0.078 |
| Beta | 42 + 7 | 83 + 38 | 51 + 24 | 0.464 |

TABLE 7

| | Addition of 3-GPA to Chow (mg/g): | | |
|---|---|---|---|
| | 0 (n = 4) | 2 (n = 5) | 5 (n = 5) |
| Body Weight (g) | | | |
| Initial | 42.72 ± 1.19 | 43.55 ± 1.09 | 43.02 ± 0.82 |
| Final | 45.70 ± 1.64 | 45.53 ± 0.97 | 34.97 ± 1.16*** |
| Fat Mass (g) | 13.45 ± 0.69 | 13.87 ± 0.38 | 8.65 ± 0.81** |
| Lean Body Mass (% BW) | 70.60 ± 0.78 | 69.54 ± 0.57 | 75.47 ± 1.57* |
| Diaphragm | | | |
| (mg) | 97.5 ± 2.7 | 103.9 ± 1.2 | 96.4 ± 4.2 |
| (% BW) | 0.21 ± 0.01 | 0.23 ± 0.004 | 0.28 ± 0.018** |
| Calf Muscle | | | |
| (mg) | 133.5 ± 23.0 | 143.2 ± 5.6 | 142.5 ± 4.2 |
| (% BW) | 0.29 ± 0.05 | 0.32 ± 0.018 | 0.41 ± 0.018* |

Data are shown as means ± S.E.M. Statistical analysis was performed by analysis of variance.
P-values for comparison to control mice: *, $P < 0.05$. , $P < 0.01$. *, $P < 0.001$.

TABLE 8

| | Insulin Sensitivity Index | | Body Wt. (kg) | |
|---|---|---|---|---|
| Subject | Placebo | 3-GPA | Pre-Tx | 3-GPA |
| Monkey 606 | 0.0040 | 0.0058 | 6.6 | 6.1 |
| Monkey 11 | 0.0063 | 0.0076 | 5.5 | 5.2 |
| Monkey 17 | 0.0070 | 0.0110 | 4.5 | 4.6 |

I claim:

1. A method of treating or preventing impaired glucose tolerance in a patient susceptible to or experiencing impaired glucose tolerance comprising the systemic administration to said patient of an amount effective to treat or prevent impaired glucose tolerance of 3-guanidinopropionic acid or a pharmaceutically acceptable salt thereof.

2. A method of claim 1 wherein the mode of administration is oral and the patient is a human.

3. A method according to claim 1 wherein said effective amount of 3-GPA ranges from 1–100 mg/kg/day.

4. A method according to claim 1 wherein said effective amount of 3-GPA ranges from 5–100 mg/kg/day.

* * * * *